US008608953B2

(12) United States Patent
Brotherton et al.

(10) Patent No.: US 8,608,953 B2
(45) Date of Patent: Dec. 17, 2013

(54) METABOLIC DETOXIFICATION SYSTEM AND METHOD

(75) Inventors: John D. Brotherton, Cardiff by the Sea, CA (US); Dar He, San Diego, CA (US)

(73) Assignee: Vital Therapies, Inc., San Diego, CA (US)

(*) Notice: Subject to any disclaimer, the term of this patent is extended or adjusted under 35 U.S.C. 154(b) by 74 days.

(21) Appl. No.: 13/361,812

(22) Filed: Jan. 30, 2012

(65) Prior Publication Data

US 2012/0197174 A1 Aug. 2, 2012

Related U.S. Application Data

(62) Division of application No. 11/064,566, filed on Feb. 23, 2005, now Pat. No. 8,105,491.

(60) Provisional application No. 60/565,888, filed on Apr. 27, 2004.

(51) Int. Cl.
*A61M 1/36* (2006.01)
*B01D 61/18* (2006.01)
*B01D 61/20* (2006.01)
*B01D 63/02* (2006.01)

(52) U.S. Cl.
USPC ......... 210/96.2; 210/85; 210/188; 210/195.2; 210/196; 210/259; 210/500.23; 210/500.42; 422/44; 422/48; 435/286.1; 435/286.6; 435/297.1; 604/6.09; 604/6.11; 604/19

(58) Field of Classification Search
USPC ......... 210/85, 86, 96.2, 137, 188, 195.2, 196, 210/181, 182, 258, 259, 198.1, 321.6, 210/321.65, 321.72, 500.23, 500.42, 645, 210/646, 650, 651, 739, 743, 805, 806; 422/44–48; 604/4.01, 5.01, 6.01, 6.09, 604/6.11, 19, 27; 435/286.1, 286.6, 297.1
See application file for complete search history.

(56) References Cited

U.S. PATENT DOCUMENTS

| 3,878,564 | A | | 4/1975 | Yao et al. |
| 4,714,556 | A | | 12/1987 | Ambrus et al. |
| 4,828,547 | A | * | 5/1989 | Sahi et al. ..................... 604/110 |
| 4,897,184 | A | * | 1/1990 | Shouldice et al. .............. 210/87 |
| 4,950,225 | A | * | 8/1990 | Davidner et al. ............ 604/6.08 |

(Continued)

FOREIGN PATENT DOCUMENTS

| CN | 1352992 | 6/2002 |
| JP | 10-234850 A | 9/1998 |

(Continued)

OTHER PUBLICATIONS

European Search Report (ESR) from EP 05 71 4053.

(Continued)

*Primary Examiner* — Joseph Drodge
(74) *Attorney, Agent, or Firm* — DLA Piper LLP (US)

(57) ABSTRACT

An extracorporeal filtration and detoxification system and method generally comprise separating ultrafiltrate from cellular components of blood, treating the ultrafiltrate independently of the cellular components in a recirculation circuit, recombining treated ultrafiltrate and the cellular components, and returning whole blood to the patient. A recirculation circuit generally comprises an active cartridge including active cells operative to effectuate a selected treatment; in some embodiments, the active cells are the C3A cell line.

53 Claims, 5 Drawing Sheets

(56) References Cited

U.S. PATENT DOCUMENTS

| | | | |
|---|---|---|---|
| 4,978,616 A * | 12/1990 | Dean et al. | 435/70.3 |
| 5,277,820 A | 1/1994 | Ash | |
| 5,290,684 A | 3/1994 | Kelly | |
| 5,368,555 A | 11/1994 | Sussman et al. | |
| 5,891,713 A | 4/1999 | Liu et al. | |
| 5,919,369 A * | 7/1999 | Ash | 210/645 |
| 6,241,945 B1 * | 6/2001 | Owen | 422/44 |
| 6,561,997 B1 * | 5/2003 | Weitzel et al. | 604/6.09 |
| 6,746,607 B1 | 6/2004 | Vijayalakshmi et al. | |
| 6,913,588 B2 | 7/2005 | Weitzel et al. | |
| 7,160,719 B2 | 1/2007 | Nyberg | |
| 7,169,303 B2 * | 1/2007 | Sullivan et al. | 210/321.63 |
| 7,942,842 B2 | 5/2011 | Della Torre | |
| 8,105,191 B2 * | 1/2012 | Toyoda et al. | 474/28 |
| 8,105,491 B2 * | 1/2012 | Brotherton et al. | 210/639 |
| 2001/0056185 A1 | 12/2001 | Lee | |
| 2003/0017142 A1 | 1/2003 | Toner et al. | |
| 2004/0024342 A1 | 2/2004 | Weitzel et al. | |
| 2005/0182349 A1 | 8/2005 | Linde et al. | |
| 2005/0186664 A1 * | 8/2005 | Rosen et al. | 435/69.7 |

FOREIGN PATENT DOCUMENTS

| | | |
|---|---|---|
| WO | WO 91/18087 A1 | 11/1991 |
| WO | WO 99/37335 A1 | 7/1999 |
| WO | WO 00/64510 A1 | 11/2000 |
| WO | WO 2004/014315 A2 | 2/2004 |

OTHER PUBLICATIONS

U.S. Appl. No. 60/541,533, filed Feb. 2, 2004, Linde and Williams.

Allen et al., "Advances in Bioartificial Liver Devices," *Hepatology* (2001), 447-455, The American Association for the Study of Liver Diseases.

Awad et al., "Results of a Phase I Trial Evaluating a Liver Support Device Utilizing Albumin Dialysis," *Surgery* (2001), 130(2):354-362, Mosby, Inc.

De Vriese et al., "Cytokine Removal during Continuous Hemofiltration in Septic Patients," *J. Am. Soc. Nephrol.* (1999), 10:846-853, The American Society of Nephrology.

"Deaths and Hospitalizations from Chronic Liver Disease and Cirrhosis—United States, 1980-1989," *MMWR Morb. Mortal. Wkly. Rep.* (1993), 41(52,53):969-973, U.S. Department of Health and Human Services.

Detry et al., "Clinical Use of a Bioartificial Liver in the Treatment of Acetaminophen-Induced Fulminant Hepatic Failure," *Am. Surg.* (1999) 65(10):934-938.

Ellis et al., "Pilot-Controlled Trial of the Extracorporeal Liver Assist Device in Acute Liver Failure," *Hepatology* (1996), 24(6)1446-1451, The American Association for the Study of Liver Diseases.

Ferenci, Peter, "Pathogenesis of Hepatic Encephalopathy," (2006), 13 pages, UpToDate.

Forsythe et al., "Sodium Bicarbonate for the Treatment of Lactic Acidosis," *CHEST* (2000), 117(1):260-267.

Kellum et al., "Diffusive vs. Convective Therapy: Effects on Mediators of Inflammation in Patients with Severe Systemic Inflammatory Response Syndrome," *Crit. Care Med.* (1998), 26(12):1995-2000, Lippincott Williams & Wilkins.

Kim et al., "Burden of Liver Disease in the United States: Summary of a Workshop," *Hepatology* (2002), 36(1):227-242.

Kjaergard et al., "Artificial and Bioartificial Support Systems for Acute and Acut-on-Chronic Liver Failure: A Systematic Review," *JAMA* (2003), 289(2):217-222, American Medical Association.

Levraut et al., "Effect of Continuous Venovenous Hemofiltration with Dialysis on Lactate Clearance in Critically Ill Patients," *Crit. Care Med.* (1997), 25(1):58-62, Williams & Wilkins.

Maxvold et al., "Amino Acid Loss and Nitrogen Balance in Critically Ill Children with Acute Renal Failure: A Prospective Comparison between Classic Hemofiltration and Hemofiltration with Dialysis," *Crit. Care Med.* (2000), 28(4):1161-1165.

Millis et al., "Initial Experience with the Modified Extracorporeal Liver-Assist Device for Patients with Fulminant Hepatic Failure: System Modifications and Clinical Impact," *Transplantation* (2002), 74:1735-1746, Lippincott Williams & Wilkins, Inc.

Mitzner et al., "Extracorporeal Detoxification Using the Molecular Adsorbent Recirculating System for Critically Ill Patients with Liver Failure," *J. Am. Soc. Nephroi.* (2001), 12:S75-S82, The American Society of Nephrology.

Nyberg and Misra, "Hepatocyte Liver-Assist Systems—a Clinical Update," *Mayo Clin. Proc.* (1998), 73:765-771.

Olson et al., "Principals of Liver Support Systems," (1999), 14 pages, http://biomed.brown.edu/Courses/BI108/BI108_1999_Groups/Liver_Team/Liver.html.

Patzer II et al., "Novel Bioartificial Liver Support System: Preclinical Evaluation," in David Hunkeler et al. (eds.), Bioartificial Organs II Technology, Medicine, and Materials, *Ann. NY Acad. Sci.* (1999), 875:340-352, The New York Academy of Sciences.

Patzer II et al., "Preclinical Evaluation of the Excorp Medical, Inc. Bioartificial Liver Support System," *J. Am. Coll. Surg.* (2002), 195(3):299-310, Elsevier Science Inc.

Pazzi et al., "Serum Bile Acids in Patients with Liver Failure Supported with a Bioartificial Liver,"*Aliment. Pharmacol. Ther.* (2002), 16:1547-1554, Blackwell Science Ltd.

Sauer et al., "Development of a Hybrid Liver Support System," *Ann. NY Acad. Sci.* (2001), 308-319.

Stevens, A. Christopher, "Liver Support Systems," *UpToDate* (2006), 9 pages.

Strain and Neuberger, "A Bioartificial Liver—State of the Art," *Science* (2002) 295:1005-1009.

Sussman et al., "Extracorporeal Liver Support," *J. Clin. Gastroenterol.* (1994), 18(4):320-324, Raven Press, Ltd., New York.

Wang et al., "Comparison of Porcine Hepatocytes with Human Hepatoma (C3A) Cells for Use in a Bioartificial Liver Support System," *Cell Transplant.* (1998), 7(5):459-468, Elsevier Science Inc.

* cited by examiner

METABOLIC DETOXIFICATION SYSTEM AND METHOD

CROSS REFERENCE TO RELATED APPLICATIONS

This application is a divisional application of U.S. application Ser. No. 11/064,566 filed Feb. 23, 2005, now issued as U.S. Pat. No. 8,105,491; which claims the benefit under 35 USC §119(e) to U.S. Application Ser. No. 60/565,888 filed Apr. 27, 2004. The disclosure of each of the prior applications is considered part of and is incorporated by reference in the disclosure of this application.

BACKGROUND OF THE INVENTION

1. Field of the Invention

The present invention relates generally to metabolic detoxification, and more particularly to an extracorporeal blood filtration and detoxification system and method employing a recirculation circuit.

2. Background Information

The processing of blood has been performed to remove a variety of blood constituents for therapeutic purposes. Examples of blood processing methods include hemodialysis that allows to remove metabolic waste products from the blood of patients suffering from inadequate kidney function. Blood flowing from the patient is filtrated to remove these waste products, and then returned to the patient. The method of plasmapheresis also processes blood using tangential flow membrane separation, to treat a wide variety of disease states. Membrane pore sizes can be selected to remove the unwanted plasma constituents. Blood can be also processed using various devices utilizing biochemical reactions to modify biological constituents that are present in blood. For instance, blood components such as bilirubin or phenols can be gluconized or sulfated by the in vitro circulation of blood plasma across enzymes that are bonded to membrane surfaces.

Various techniques, such as centrifugation, have been available for washing blood cells prior to returning them to the patient. In such techniques a centrifuge is used for separating and washing the red cells in batches. This is a relatively slow process, the apparatus for performing which can be complex and expensive.

Presently used technologies are generally deficient with respect to supporting patients with compromised liver function, for example. Conventional systems and methods suffer from various problems associated with sustaining such patients until a suitable donor organ can be found for transplantation or until the patient's native liver can regenerate to a healthy state.

SUMMARY OF THE INVENTION

Embodiments of the present invention overcome the foregoing and various other shortcomings of conventional technology, providing an extracorporeal blood filtration and detoxification system and method employing a recirculation circuit.

In accordance with one aspect of the present invention, a system and method provide liver support for multiple therapeutic applications related to acute liver disease, allowing for either the potential regeneration of the impaired or partial liver to a healthy state, or the support of the patient with acute liver failure until all or part of a suitable donor organ can be found for transplant.

DETAILED DESCRIPTION OF THE INVENTION

The following terminology, definitions and abbreviations apply:

The term "active cartridge" refers to a hollow fiber based cartridge comprising cells (such as, for example, the C3A cell line) having utility in therapeutic applications and detoxification processes.

The term "blood circuit" refers to a circuit of tubing connected to a double lumen catheter and operative to circulate blood from a patient to a blood control unit and back to the patient.

The term "C3A cell line" refers to a sub-clone of the human hepatoblastoma cell line HepG2. In some embodiments, C3A cells may be contained in the extracapillary space of one or more active cartridges. An example of the external organ assist device which is preferably used with the system is a cell line commercially available from Baylor College of Medicine and designated as C3A. This cell line has been deposited at the American Type Culture Collection under ATCC No. CRL-10741.

The term "detoxification device" refers to a cartridge, canister, or other device that provides a means of removal of specific or non-specific molecules from a fluid stream. Examples would be a dialysis cartridge, an adsorption cartridge, or a filter.

The term "extracapillary space" (ECS) refers to space outside the hollow fibers of active cartridges or an ultrafiltrate generator. The ECS of active cartridges may generally house the C3A cells.

The term "intracapillary space" (ICS) refers to space inside the hollow fibers of active cartridges or an ultrafiltrate generator. The ICS is the flow path for whole blood or the ultrafiltrate fluid.

The term "recirculation circuit" refers to a circuit generally enabling filtration, detoxification, and treatment of ultrafiltrate fluid; in some implementations, a recirculation circuit generally encompasses a reservoir, an oxygenator, and one or more active cartridges.

The term "transmembrane pressure" (TMP)" refers to pressure across the membrane. In particular, within the ultrafiltrate generator or other membranous cartridge, the mean pressure in the ICS minus the mean pressure in the ECS. The amount of ultrafiltration may generally be determined by the TMP across the cartridge membrane; accordingly, TMP and the amount and rate of ultrafiltration may generally be a function of the operational characteristics of an ultrafiltrate pump as well as various physical properties (e.g., pore size and surface area) of the membrane employed in the ultrafiltrate generator.

The term "ultrafiltrate" (UF) refers to plasma fluid and dissolved macromolecules filtered across the semi-permeable membrane of an ultrafiltrate generator.

The term "ultrafiltrate generator" (UFG) refers to a device comprising or embodied as a "blank" active cartridge (i.e., a hollow fiber cartridge which does not contain therapeutically active cells) and operative to separate plasma fluid (ultrafiltrate) from cellular blood components. The hollow fibers may be composed of a semi-permeable membrane which has, for example, a nominal molecular weight cut-off of approximately 100,000 Daltons in some implementations. During use of the UFG, blood may be circulated through the ICS of the hollow fibers; ultrafiltrate, comprising blood plasma and various macromolecules, passes through the membrane fiber walls into the recirculation circuit, where it is circulated through one or more active cartridges.

The term "ultrafiltration" refers generally to a process during which ultrafiltrate is pulled from whole blood across the semi-permeable membrane of the UFG. In some embodiments described below, an ultrafiltrate pump may control the rate of ultrafiltrate production, while the pore size of the hollow fiber membrane of the UFG may control the amount of ultrafiltrate permeating the membrane.

EMBODIMENTS OF THE INVENTION

Figure 1:
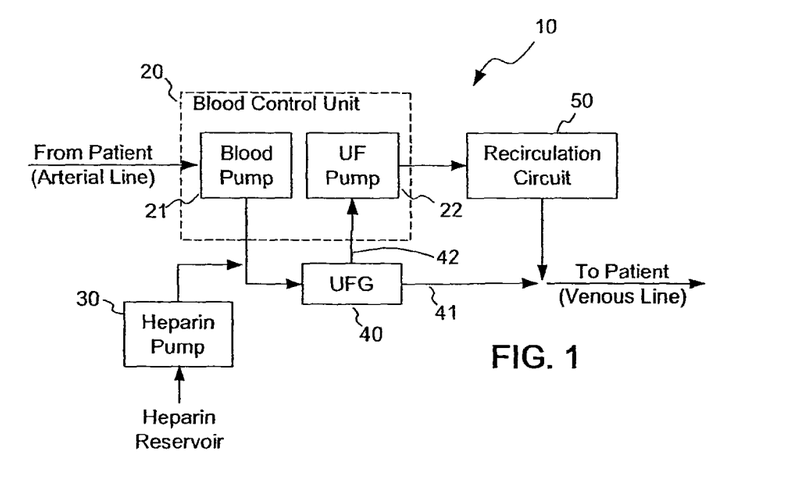
FIG. 1 is a simplified block diagram illustrating one embodiment of an extracorporeal filtration and detoxification system.

Turning now to the drawings, FIG. 1 is a simplified block diagram illustrating one embodiment of an extracorporeal filtration and detoxification system. As indicated in FIG. 1, system 10 generally comprises a blood control unit 20, a heparin pump 30, an ultrafiltrate generator UFG 40, a recirculation circuit 50, and can optionally include other detoxification devices. In the exemplary FIG. 1 implementation, system 10 embodies a continuous therapy device generally operable to draw blood (facilitated by a blood pump 21, for example) from a patient into blood control unit 20 via an appropriate conduit or other device such as a double lumen catheter, for instance, or the equivalent thereof.

In operation, UFG 40 may receive whole blood from blood pump 21 and separate UF fluid from cellular components substantially as set forth below. While cellular components may be returned from UFG 40 to the patient (as indicated by conduit or fluid line 41, for example) via the venous access, UF may be drawn from UFG 40 (as indicated by conduit or fluid line 42, for example) by an ultrafiltrate pump 22 for redirection through recirculation circuit 50. Following treatment in recirculation circuit 50, UF may be recombined with cellular components for reintroduction to the patient.

As illustrated by the embodiment shown on FIG. 1, a heparin infusion pump 30 can be used to introduce heparin into the whole blood upstream of UFG 40. Those of skill in the art will appreciate that heparin, an acidic mucopolysaccharide, or various derivatives thereof may provide anticoagulant effects; other anticoagulant agents may be appropriate depending upon, among other things, the nature of the detoxification treatment and various other system parameters.

Figure 2:
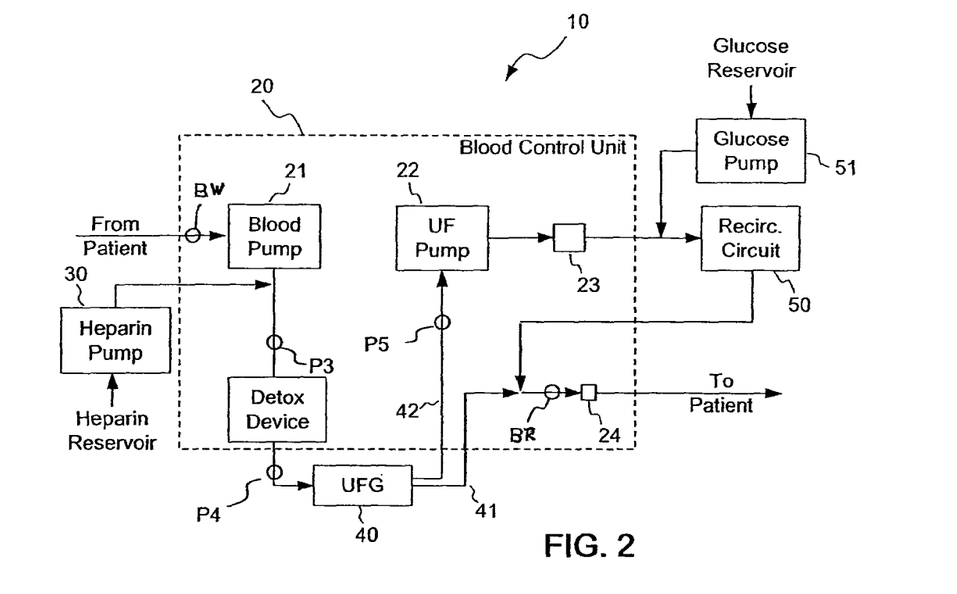
FIG. 2 is a simplified block diagram illustrating one embodiment of a blood control unit operative in conjunction with a recirculation circuit.

FIG. 2 is a simplified block diagram illustrating one embodiment of a blood control unit operative in conjunction with a recirculation circuit. Overall operation of system 10 and the various components thereof may generally correspond to that set forth above with reference to FIG. 1.

Blood control unit 20 as contemplated herein may be a dual pump continuous dialysis-type machine; in that regard, blood control unit 20 may be embodied, for example, in a Diapact™ CRRT (Continuous Renal Replacement Therapy) Machine such as manufactured by B. Braun. Various alternatives exist, however, and proprietary hardware may be constructed in accordance with the present disclosure. Those of skill in the art will appreciate that the constitution of blood control unit 20 is susceptible of alterations and alternative embodiments. Additionally, a detoxification cartridge (or cartridges), may be placed in various places within the blood and ultrafiltrate circuits.

In an exemplary embodiment, blood control unit 20 may comprise two pumps (blood pump 21 and UF pump 22) as noted above. Blood pump 21 may enable circulation of a patient's whole blood through UFG 40 and facilitate return of cellular blood components to the patient, for example, through line 41. In operation, UF pump 22 may draw UF from UFG 40 (e.g., through line 42 as noted above) and deliver the UF to recirculation circuit 50; in addition to supplying recirculation circuit 50, UF pump 22 may assist with recombination of treated UF with the cellular components of a patient's blood by maintaining a predetermined or dynamically adjusted hydrostatic head, for example.

As set forth above, heparin infusion pump 30 may provide heparin or a similar anticoagulation agent to the blood circuit upstream of UFG 40; similarly, a glucose infusion pump 51 may provide a supply of glucose to the UF upstream of recirculation circuit 50 to nourish the C3A or other active cells. In some embodiments, heparin pump 30 and glucose pump 51 may comprise or be implemented in Harvard Ohmeda Dual Syringe Pumps, for example, or equivalents thereof. Pumps 30 and 51 are illustrated in representative form only; irrespective of the type of pumping apparatus implemented, pumps 30 and 51 may deliver fluid at a predetermined constant rate, for example, or at a dynamically adjustable rate. In some embodiments, for instance, pumps 30 and 51 may comprise suitable sensors or sensor inputs, actuators, and control electronics operative in accordance with sensor output and control signals to adjust flow rates dynamically as a function of overall flow rate through blood control unit 20 and recirculation circuit 50, respectively. Indications of overall flow rate may be obtained, for example, from output provided by flow rate or pressure sensors distributed at various locations in the circuits substantially as set forth below.

An exemplary embodiment shown by FIG. 2 includes five fluid pressure transducers generally operative to detect absolute value as well as variances or perturbations in fluid pressures throughout the tubing system of blood control unit 20. Additionally or alternatively, fluid flow meters may be incorporated at similar or equivalent points in the indicated flow stream. Each pressure transducer in the FIG. 2 embodiment may be covered or sheathed by a respective transducer protector as is generally known in the art. Additional pressure sensors may be located throughout the circuit to measure and control the fluid flow paths.

Blood withdrawal pressure may be measured as indicated at point BW. The blood withdrawal monitors fluid pressure and any pressure fluctuations of the outflow of blood from a patient to blood pump 21. Blood pump discharge pressure may be measured as indicated at point P3. The blood pump discharge pressure sensor monitors the inlet pressure of the next distal component to the blood pump, and any fluctuations or variations thereof. Blood return pressure may be measured as indicated at point BR. As shown by FIG. 2, the blood return sensor monitors both the outlet pressure of the component immediately proximal as well as the fluid pressure of the inflow of whole blood back to the patient.

In some embodiments, blood control unit 20 may also comprise a blood leak detector 23 and one or more valve assemblies 24. Blood leak detector 23 may be located within the UF line (e.g., downstream of UF pump 22 as depicted in FIG. 2), and may be operative to identify whole or hemolyzed blood present in the UF fluid. The presence of such whole blood or other cellular constituents may evidence a failure or degradation of UFG 40 efficacy, and may generally indicate a need to replace, clean, or otherwise to maintain the hollow fiber cartridge implemented at UFG 40.

Valve assembly 24 may be embodied in any of various control valves or other fluid regulation apparatus generally known in the art. In some embodiments, valve assembly 24 may be a safety or one-way valve, permitting only unidirectional fluid flow to a patient; in this implementation, upstream pressure fluctuations may not create negative pressure or suction at the venous access of the patient. Additionally, valve assembly 24 may be selectively or dynamically activated responsive to control signals or sensor input (e.g., from pressure or flow sensors at point PV or at other locations in blood control unit 20) such that fluid flow may be regulated at or near a constant rate as upstream pressures vary over time, or shut off completely.

As noted above, UFG 40 generally comprises one or more "blank" hollow fiber cartridges operative to separate UF from cellular components of the whole blood drawn from a patient. Those of skill in the art will appreciate that some therapeutic implementations may realize increased efficiency or efficacy where UFG 40 is primed before use; in that regard, a priming solution (such as saline, for example) may be provided to UFG 40 either before, in conjunction with, or after installation into system 10. Alternative methods can be used for plasma separation, if desired. For example, centrifugation can be used.

As illustrated in FIG. 2, UFG 40 may be implemented as an independent system component, i.e., distinct or physically separated from blood control unit 20; in the exemplary embodiment, independent maintenance, repair, or substitution of blood control unit 20, UFG 40, or constituent parts thereof, for example, may be facilitated by the fact that each is implemented as a discrete component of system 10. In an alternative embodiment, UFG 40 may be incorporated into or integral with blood control unit 20; this embodiment may provide advantages attendant with shorter or more direct fluid flow through cartridges employed at UFG 40, and accordingly, may reduce power consumption and increase overall system efficiency. In the alternative embodiment, hollow fiber filter cartridges implemented at UFG 40 may be configured to allow easy removal and replacement with respect to blood control unit 20.

Additionally, it is noted that air detectors may be implemented to detect air bubbles or other gaseous contaminants within the circulating fluids. In some embodiments, for example, one or more air detectors may be incorporated into the blood circuit at selected locations in blood control unit 20, and one or more additional air detectors may also be incorporated at selected locations in recirculation circuit 50. As is generally known and practiced in the art, numerous suitable mechanical filtration systems may be employed to remove unwanted gaseous contamination. In some embodiments, one or more of such filtration systems may be selectively operative responsive to output from one or more air detectors. Accordingly, while representation of some of the hardware has been omitted for clarity, it will be appreciated that the present disclosure contemplates detection and removal of air and other gaseous bubbles from the fluidic system, particularly at or near venous access to the patient.

Figure 3:
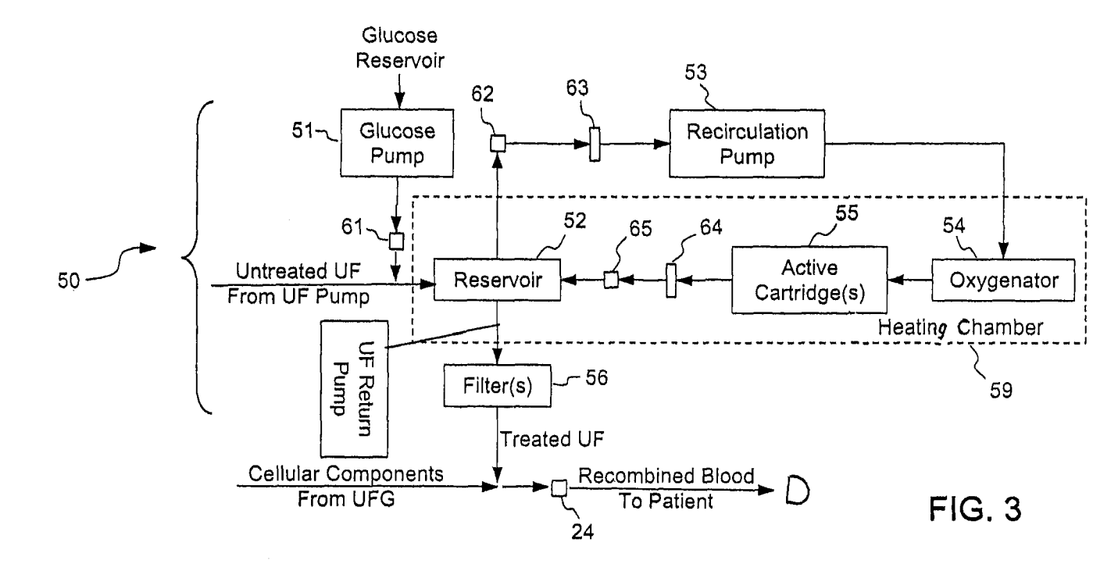
FIG. 3 is a simplified block diagram illustrating one embodiment of a recirculation circuit.

FIG. 3 is a simplified block diagram illustrating one embodiment of a recirculation circuit. In the FIG. 3 embodiment, recirculation circuit 50 is generally fed by glucose infused UF; in that regard, output from UF pump 22 (i.e., untreated UF) may be infused with glucose or a similar substance from glucose pump 51 through a valve assembly 61 or other flow regulation device prior to, or in conjunction with, introduction into recirculation circuit 50.

As noted above with reference to valve assembly 24, valve assembly 61 may permit only unidirectional fluid flow (i.e., from pump 51 to the UF line) such that pressure fluctuations do not draw UF from the line and into pump 51. As set forth above with reference to FIG. 2, valve assembly 61 may be selectively or dynamically activated responsive to control signals or sensor input (e.g., from pressure or flow sensors at selected locations in recirculation circuit 50) such that glucose may be delivered at a predetermined constant rate, for example, or at a dynamically adjustable rate as a function of overall flow rate through recirculation circuit 50.

The exemplary recirculation circuit 50 generally comprises a recirculation pump 53, an oxygenator 54, one or more active cartridges 55 or clusters of cartridges, and a reservoir 52. The recirculation circuit may optionally contain one or more detoxification devices D, as shown by FIG. 3. As represented by the dashed box in FIG. 3, oxygenator 54, active cartridges 55, and reservoir 52, or some combination thereof, may be disposed in a heating chamber 59 or other environmentally controlled room or space. Additionally, recirculation circuit 50 may include one or more additional filters 56 interposed between reservoir 52 and the point at which treated UF is recombined with cellular components from UFG 40. A UF return pump may be used to deliver ultrafiltrate through the filter, or filters. If desired, the locations of oxygenator 54 and active cartridges 55 can be optionally switched.

As indicated in FIG. 3, untreated UF output from UF pump 22 may be directed to reservoir 52 following glucose infusion. In some embodiments, reservoir 52 may comprise or be implemented as an arterial filter such as manufactured by Sorin, for example. In that regard, reservoir 52 may generally serve as a holding tank or container, storing sufficient UF to account for any difference in flow rates between the blood circuit in blood control unit 20 and recirculation circuit 50. A level sensor and control or a weighing system may be used to maintain fluid balance in the recirculation circuit.

Recirculation pump 53 may be embodied in a peristaltic pump such as manufactured by Watson Marlow, for example, or any other suitable shaft driven pumping mechanism such as those employing reciprocating pumps, centrifugal pumps, and the like. In operation, recirculation pump 53 may drive circuit 50, drawing UF from reservoir 52, circulating the UF fluid through oxygenator 54 and active cartridges 55 and back into reservoir 52. Other pumping systems can be used if desired. For example, the blood and UF pumping system COBE CV Stockert SIII can be used.

Oxygenator 54 may comprise, or be embodied in, any of various membrane oxygenators generally known in the art or other types of oxygenators developed and operative in accordance with known principles. In operation, oxygenator 54 may provide oxygen for utilization in the detoxification or therapeutic process executing in active cartridges 55. Accordingly, the type, nature, and operational characteristics of oxygenator 54 may be selected as a function of the type and quantity of active cells (such as C3A cells, for example) maintained within active cartridges 55, UF flow rate through recirculation circuit 50, and other system parameters. In some implementations employing C3A cells, for example, oxygenator 54 may be embodied in a Monolyth M™ oxygenator such as manufactured by Sorin.

Similarly, heating chamber 59 may comprise or implement any number of environmental control apparatus known in the art and generally operative to maintain selected environmental operating conditions for oxygenator 54, active cartridges 55, and reservoir 52. For example, some implementations may benefit from maintaining the foregoing system components at a constant 37° C., or within a predetermined or specified range close to that temperature. It will be appreciated that optimum temperatures, temperature ranges, and acceptable deviations therefrom may be influenced by the type and quantity of active cells implemented in active cartridges 55, ambient conditions and overall UF flow rates through recirculation pump 53, the nature and character of treatment or processes occurring in active cartridges 55, and the like. In some embodiments, recirculation circuit 50 incorporates a Certomat™ heating chamber apparatus manufactured by B. Braun.

As set forth above, recirculation circuit 50 may incorporate one or more active cartridges 55, each of which may be embodied as or comprise a hollow fiber filter. Accordingly, each active cartridge 55 may comprise a bundle of hollow fibers employing a semi-permeable membrane. Surrounding these fibers, in the ECS, one or more types of active cells may be utilized to treat the UF in a selected manner as the UF circulates through the ICS. The character, quantity, density, and genetic composition of active cells facilitating treatment in active cartridges 55 may be selected as a function of the overall functionality of system 10 in which recirculation circuit 50 is employed. As set forth herein, an exemplary embodiment of system 10 and recirculation circuit 50 incorporates C3A cells, though other alternatives exist, depending upon, inter alia, the desired utility of system 10 and the nature of the contaminant sought to be removed or treated.

In some embodiments, hollow fiber active cartridges 55 may have a nominal molecular weight cut-off of greater than 70,000 Daltons, for example, allowing middle molecular weight molecules such as albumin to cross the membrane. Macromolecules produced by the C3A or other active cells may be able to diffuse into the UF circulating through the ICS; similarly, albumin-carrying toxins are able to diffuse from the ICS to the active cells occupying the ECS. Where active cartridges 55 comprise more than one of the mechanisms described above, multiple cartridges may be employed in parallel, for example, or in series.

During clinical or therapeutic treatment, UF may be pumped through the lumen (ICS) of the hollow fiber cartridge, allowing toxins, nutrients, glucose, and dissolved oxygen from the UF to diffuse across the membrane into the ECS, where the active cells may metabolize them. Metabolites, along with albumin and other proteins produced by the cells, may diffuse back across the membrane into the UF for return to the patient.

As indicated in FIG. 3, treated UF may be returned to reservoir 52. In that regard, it is noted that the relative flow rates through blood control unit 20 and recirculation circuit 50 need not be equal. Reservoir 52 may collect both untreated UF transported from UF pump 22 as well as treated UF which has already passed through active cartridges 55. Implementation of reservoir 52 as indicated may enable higher or lower flow rates through recirculation circuit 50 than through the blood circuit, as required, whereas UF may be supplied from recirculation circuit 50 downstream to the patient at a suitable rate.

During operation of system 10, UF from reservoir 52 may pass through one or more additional filters 56 or filter series prior to reintroduction to the blood circuit. In some embodiments, three in-line (i.e., arranged in series) cell filters may employ a membrane pore size of approximately 0.45 μm, for example. Additional filters 56 may provide a safety feature, preventing possible transmission of C3A or other active cells to the patient; accordingly, the pore size of membranes employed at additional filters 56 may generally be selected as a function of the type of cells utilized at active cartridges 55 or the nature and average size of other contaminants sought to be filtered. Additional filters 56 may be placed immediately upstream of the juncture of recirculation circuit 50 and the blood circuit as indicated in FIG. 3.

In operation of recirculation circuit 50 in conjunction with system 10, UF may be circulated through a series of active cartridges 55 comprising, in some embodiments, C3A cells or other active cells operative to effectuate one or more selected therapeutic treatments. Within active cartridges 55, the UF passes through the ICS of a bundle of hollow fibers, each comprising a semi-permeable membrane. The C3A or other active cells may be disposed in the ECS of active cartridges 55. The semi-permeable membrane fibers permit passage (e.g., from the active cells to the UF) of selected macromolecules and other cellular products such as albumin, transferrin, α-1-antitrypsin, α-fetoprotein, and others. Simultaneously, the semi-permeable membrane fibers permit passage of toxins and metabolic necessities (e.g., such as glucose and oxygen) from the UF to the active cells.

Following circulation through active cartridges 55 and deposition in reservoir 52, the UF may be subject to additional filtration such as by additional filters 56; as noted above, additional filtration may comprise employing three or more 0.45 μm in-line cell filters. UF may then be recombined with the cellular components of the patient's blood in the blood circuit. The recombined whole blood and UF may be returned to the patient through the double lumen catheter, regulated by valve assembly 24 substantially as set forth above. The foregoing circulation strategy may be maintained continuously for the duration of therapy facilitated by system 10 and recirculation circuit 50 utilizing active cartridges 55.

As set forth above and contemplated herein, the C3A cell line is a subclone of the human hepatoblastoma cell line HepG2, and is typically available through American Type Culture Collection (ATCC). HepG2, the parent cell line, was derived from a hepatoblastoma excised from a 15-year old Caucasian male from Argentina in 1975 in Philadelphia, Pa., USA. Some subclones of this parent cell line, such as C3A, for example, exhibit such liver-specific functional capabilities as high albumin production, α-fetoprotein (AFP) production, and growth in serum free medium. The C3A cell line has demonstrated such liver-specific functionality, and has been described herein by way of example only, and not by way of limitation. In that regard, it is noted that the utility of system 10, recirculation circuit 50, and the respective components thereof is described herein only by way of example; those of skill in the art will recognize that the disclosed system and method may facilitate detoxification and therapeutic treatment in contexts other than liver therapies. The present disclosure is not intended to be limited to any specific application implementing any particular cell line.

Recirculation circuit 50 may further comprise various other components as indicated in FIG. 3. Valve assemblies 62 and 65, for example, may prevent back-flow and provide regulated flow rates on the suction side and the pressure side, respectively, of recirculation pump 53. As set forth above, some embodiments may employ dynamically activated valve assemblies, which may be selectively adjusted to control flow rates precisely; appropriate sensors, such as temperature, pressure, or flow meters and associated electronics and control hardware are omitted from FIG. 3 for clarity. Those of skill in the art will appreciate that various techniques and flow control apparatus are generally known and encompassed herein.

A priming reservoir 63 may provide necessary fluid to prime, for example, recirculation pump 53 and active cartridges 55 (if required) as well as the conduits or tubing making up recirculation circuit 50; in that regard, a collection reservoir 64 may be provided downstream of active cartridges 55, for example, to collect priming fluid prior to therapy or to flush recirculation circuit 50 for maintenance. Additionally, maintenance or replacement of various components such as recirculation pump 53, for example, and active cartridges 55, in particular, may be facilitated by valves, quick-disconnect couplings, or other flow restricting mechanisms disposed at various locations in recirculation circuit 50. In some embodiments, a quick-disconnect coupling at both the upstream and downstream sides of active cartridges 55 may facilitate maintenance and significantly contribute to system flexibility. Where active cartridges 55 may quickly and easily be isolated from recirculation circuit 50, additional or replacement active cartridges 55 may be selectively inserted or substituted responsive to efficiency degradation, modification of treatment strategy, or other factors.

As set forth above, individual or combined performance specifications for each of the components of system 10 may be selected with particularity to support the biological, chemical, or other functionality of the therapeutic cells within active cartridges 55, to circulate blood and UF through the conduits at selected flow rates, and ultimately to provide the selected therapy. Accordingly, the functional characteristics of each component may be influenced by design choices made with respect to other aspects of system 10.

For example, one continuous dialysis-type machine supporting suitable therapeutic processes is the B. Braun Diapact™ CRRT machine noted above, which may provide sufficient flexibility to satisfy various system requirements with respect to blood control unit 20. In some embodiments, for example, blood pump 21 may be configured and operative to circulate blood from the patient through UFG 40 and back to the patient at a flow rate of approximately 200 mL/min during therapy, whereas UF pump 22 may deliver UF from UFG 40 to recirculation circuit 50 at a flow rate of approximately 20 mL/min during therapy. Treated UF may be recombined with whole blood for return to the patient at a similar 20 mL/min rate.

As set forth above, a continuous heparin infusion (provided by heparin infusion pump 30) may be used to provide heparin or another suitable anticoagulation agent to the blood circuit of system 10. Given the flow rates noted above, the Harvard Ohmeda dual syringe pump may provide appropriate heparin flow rates. The heparin may be infused at a constant rate into the blood circuit immediately downstream of the blood pump incorporated into the Diapact™ CRRT machine as indicated in FIGS. 1 and 2, for example. In some embodiments, the degree of anticoagulation may be monitored with the patient's Partial Thromboplastin Times (PTTs) drawn at regular intervals. Once therapy begins, a sliding scale algorithm may determine the heparin dosing and infusion rate which, as set forth in detail above, may be modified dynamically, facilitated by appropriate sensors, actuators, and control electronics, for example.

As set forth in more detail above, UFG 40 may implement a blank hollow fiber filter cartridge (i.e., one which contains neither C3A nor other active cells) operative to separate cellular components of blood from UF. The hollow fibers generally comprise a semi-permeable membrane having a nominal molecular weight cut-off of greater than about 70,000 Daltons. In some embodiments, total fluid volume in the ICS may approach approximately 95 mL, whereas total fluid volume in the ECS may be approximately 130 mL.

Based upon the foregoing system requirements, the Harvard Ohmeda dual syringe pump may be implemented as glucose pump 51, maintaining a continuous glucose infusion calculated to provide adequate glucose levels to the cells within active cartridges 55 during therapy. The glucose may be infused at a constant rate into the UF line upstream of the connection with recirculation circuit 50 as indicated in FIGS. 2 and 3, for example. Once therapy begins, a sliding scale algorithm may determine the glucose infusion rate which, as set forth in detail above, may be modified dynamically, facilitated by appropriate sensors, actuators, and control electronics, for example.

The Watson Marlow peristaltic pump mentioned above may be implemented as recirculation pump 53, providing constant UF flow from reservoir 52, through oxygenator 54 and the active cartridges 55, and back to reservoir 52. The pump may provide a flow rate sufficient to supply adequate nutrients and oxygenation to sustain the cells in active cartridges 55; in the case of the system parameters noted above, this flow rate may be approximately 2 L/min of UF flow. Accordingly, any pump capable of providing such a flow rate under the same operating conditions may be implemented.

In operation, membrane oxygenator 54 may be positioned within the recirculation circuit at a point upstream of active cartridges 55 to assure that sufficient oxygen is provided to the active cells during therapy. In accordance with some embodiments, total fluid volume of oxygenator 54 may approach approximately 300 mL. It will be appreciated that an gas flow meters (not shown) may be coupled between the gas supplies and oxygenator 54; as is generally known in the art, such gas flow meters may facilitate regulation of the amount of oxygen delivered to oxygenator 54, ensuring sufficient oxygenation to sustain the therapeutically active cells maintained in active cartridges 55.

During operation of some embodiments using C3A cells for treatment, the C3A cells may be contained within active cartridges 55 in the ECS outside of the membrane walls of the hollow fibers; membrane pore size may be selected such that the possibility of C3A cells leaving active cartridges 55 during treatment is exceedingly low. However, to add an additional measure of safety during treatment, a number (such as three or more, for example, coupled in series) of 0.45 μm Whatman Polycap TC in-line cell filters may be placed in the UF return line, immediately upstream of the point where treated UF recombines with the venous return circuit. The total fluid volume per filter may be approximately 75 mL.

System 10 may be designed to provide continuous treatment; accordingly, one or more auxiliary batteries or other uninterruptible power supplies may be provided at various locations in system 10. An example of a suitable back-up battery system comprises a Clary & ONEAC 1300, which may provide an uninterruptible power supply for approximately 40 minutes to all system components (such as pumps 21, 22, 30, 51, and 53, for example) during operation. Additionally or alternatively, each powered component of system 10 may be provided with a respective uninterruptible power supply.

System 10 generally comprises segments of tubing or conduits that make up the blood circuit and recirculation circuit 50. In addition to tubing or other suitable conduits, as noted above, collection bags or reservoirs 64,63 may be incorporated into the circuits to collect priming and shipping solutions prior to patient use, for example, or to facilitate system maintenance. In that regard, the tubing employed in the blood circuit and recirculation circuit 50 may generally be constructed in accordance with known materials and techniques to provide conduits suitable for therapeutic or clinical use.

Figures 4A, 4B:
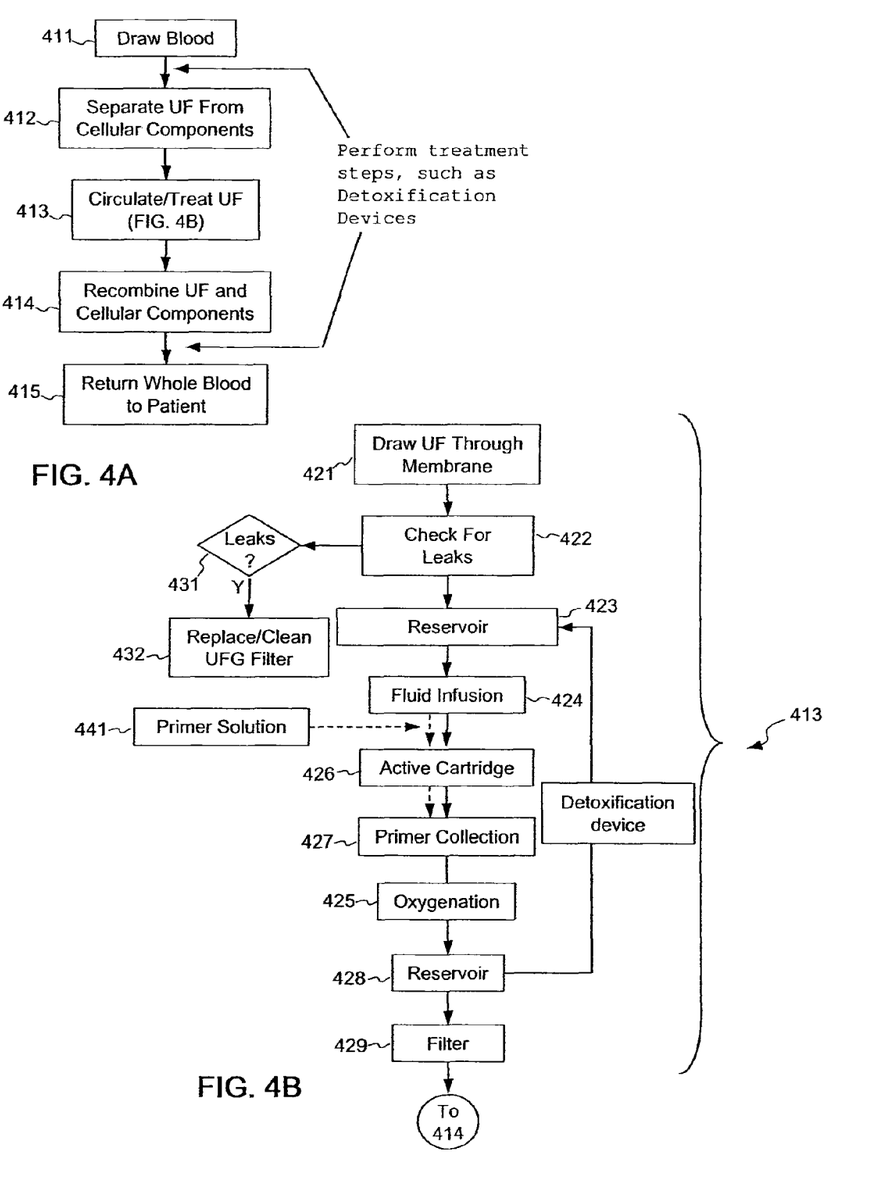
FIG. 4A is a simplified flow diagram illustrating the general operation of one embodiment of a method of extracorporeal filtration and detoxification.
FIG. 4B is a simplified flow diagram illustrating the general operation of one embodiment of a method of treating ultrafiltrate.

FIG. 4A is a simplified flow diagram illustrating the general operation of one embodiment of a method of extracorporeal filtration and detoxification. The processes depicted in FIG. 4A may be facilitated by the various components, or appropriate combinations thereof, illustrated in FIGS. 1 and 2. Initially, a method of extracorporeal filtration and detoxification of blood may begin by drawing blood from a patient as indicated at block 411. Blood may be drawn using various apparatus or devices generally known in the art, such as a double lumen catheter, for example.

Separating UF from cellular components of whole blood (as indicated at block 412, for instance) may be facilitated by an ultrafiltrate generator such as UFG 40 illustrated in FIGS. 1 and 2. As set forth in detail above with particular reference to FIG. 2, UFG 40 may be incorporated in a blood control unit 20, or may be implemented independently; in either of the foregoing embodiments, whole blood may be delivered from the patient to UFG 40 by a blood pump 21, whereas UF may be drawn through the semi-permeable membrane of UFG 40 by a dedicated UF pump 22. Though not specifically illustrated in FIG. 4A, it will be appreciated from the foregoing discussion and examination of FIGS. 1-3 that cellular components of the whole blood passing through UFG 40 may be returned to the patient, for example, through the venous access of the double lumen catheter described above.

Circulating or treating UF independently of the cellular components of whole blood (block 413) may be facilitated by a recirculation circuit such as illustrated and described in detail with reference to FIG. 3. In particular, treating UF as contemplated at block 413 generally comprises circulating the UF through one or more active cartridges containing or comprising C3A or other active cells in the ECS of a hollow fiber filter.

Recombining treated UF and the cellular components of whole blood as indicated at block 414 may utilize or involve a simple valve assembly or fluid conduit junction, for example. The recombining operation at block 414 generally represents the reintroduction of treated UF from recirculation circuit 50 to the blood circuit coursing through blood control unit 20 substantially as illustrated and described above with reference to FIGS. 1-3. In some embodiments, cellular components and treated UF may be recombined at a selected rate computed as a function of the desired rate at which whole blood is returned to the patient.

Returning whole blood to the patient as indicated at block 415 may involve utilizing valve assemblies or otherwise regulating the flow rate in accordance with the patient's physical condition and internal blood pressure requirements. As set forth above, the returning operation at block 415 may employ or comprise some or all of the following features or hardware: dynamically adjustable valve assemblies enabling precise pressure control or flow regulation; safety valves or back flow restrictors preventing upstream pressure variations from reversing the direction of blood flow; and gas bubble detection and removal apparatus or devices.

FIG. 4B is a simplified flow diagram illustrating the general operation of one embodiment of a method of treating ultrafiltrate. The processes depicted in FIG. 4B are related to operation of recirculation circuit 50, for example, and accordingly may be facilitated by the various components, or appropriate combinations thereof, illustrated in FIG. 3. Treating UF in accordance with the FIG. 4B method generally relates to the operation depicted at block 413 of FIG. 4A.

In that regard, drawing UF through a membrane as indicated at block 421 may represent an aspect of generating UF, such as with UFG 40, for example; accordingly, the drawing operation of block 421 may also be associated with the separating operation of block 412 in FIG. 4A. The process at block 421 is included in FIG. 4B for the sake of clarity and thoroughness.

Following ultrafiltration as described above, UF may be checked or analyzed for leaks. Specifically, a blood leak detector 23 (FIG. 2) may be located within the UF line downstream of UFG 40. Checking for leaks as indicated at block 422 and decision block 431 generally comprises analyzing the composition of UF downstream of UFG 40 and identifying whole or hemolyzed blood present in the UF fluid. As set forth above, the presence of such whole blood or other cellular constituents in the UF may indicate a need to replace, clean, or otherwise to maintain (block 432) the hollow fiber cartridge implemented at UFG 40.

Untreated UF input to recirculation circuit 50 may be provided to reservoir 52 as indicated at block 423. Infusion of fluid (block 424) may represent introduction of glucose or other nutrients, heparin or other anticoagulation agents, or other fluids into recirculation substantially as set forth above. It will be appreciated that the operation depicted at block 424 may occur prior to blocks 422 or 423, for example, or elsewhere in the FIG. 4B embodiment. In that regard, more than one fluid infusion may occur at selected locations throughout recirculation circuit 50 of FIG. 3 (and thus at various locations in FIG. 4B) depending upon the type and quantity of fluid to be infused, the nature and requirements of the active cells maintained in active cartridges, overall flow rate of UF through the circuit, and other system parameters.

Similarly, introduction of primer solution at block 411 and the collection of primer solution at block 427 may occur where indicated or elsewhere in FIG. 4B, depending, for example, upon the particular system components requiring priming. If reservoir 52 requires priming in the FIG. 3 embodiment, for instance, priming at block 441 may occur prior to providing UF to reservoir 52 at block 423. Valve assemblies, quick-disconnect couplings, collection bags, or other apparatus enabling primer collection at block 427 may be selectively located in recirculation circuit 50 as a function of the particular arrangement or relative orientation of system components. Accordingly, the operations at block 441 and block 427 may be duplicated or relocated in the FIG. 4B embodiment, depending upon the number and relative locations of system components (e.g., such as pump 53, oxygenator 54, and active cartridges 55) requiring priming.

UF may be oxygenated at block 425 and treated at block 426. Various aspects of the oxygenation process (e.g., pressure, partial pressures and composition of any air/gas mixture, infusion rates, and the like) at block 425 may be influenced by the quantity, density, nature, and functionality of the active cells (such as C3A cells, for example) maintained in the active cartridges and executing the treatment process at block 426. In that regard, treating or detoxifying UF may generally occur in active cartridges at block 426. As set forth in detail above, the operational characteristics and specific chemical, biological, and other processes associated with block 426 may be influenced by the intended overall operation of system 10 (i.e., the type of treatment required), and may be selectively adjusted, controlled, or otherwise manipulated in accordance with the specific hardware components implemented in recirculation circuit 50.

Treated UF may be returned to reservoir 52 as indicated at block 428 and described in detail above. Providing (block 423) and returning (block 428) UF to such a reservoir or other fluid container at both ends of a recirculation circuit 50 may allow or enable a system and method of treating UF to operate at a different flow rate than that maintained in the blood circuit of a treatment system 10.

Prior to recombining treated UF with cellular blood components at block 414, additional filtering may be conducted at block 429. In some embodiments described above, filtering at block 429 may include passing UF through one or more in-line (i.e., arranged in series) cell filters, each having a membrane pore size of approximately 0.45 μm, for example. Additionally or alternatively, filtering at block 429 may comprise passing UF through hollow fiber cartridges having very small pore sizes (such as 0.1-0.2 μm, for example), ammonia traps, charcoal filters, mechanical filters, and the like. The specific hardware or filtering apparatus selected for the block 429 operation may generally be influenced or dictated by the type of cells utilized at active cartridges 55 or the nature and average size of other contaminants sought to be filtered. Filtering at block 429 may occur immediately upstream of the juncture of recirculation circuit 50 and the blood circuit as indicated in FIG. 3. It will be appreciated that UF which is neither processed at block 429 nor returned to the patient may be recirculated for additional treatment as represented by the loop from block 428 back up to block 423.

Figure 5:
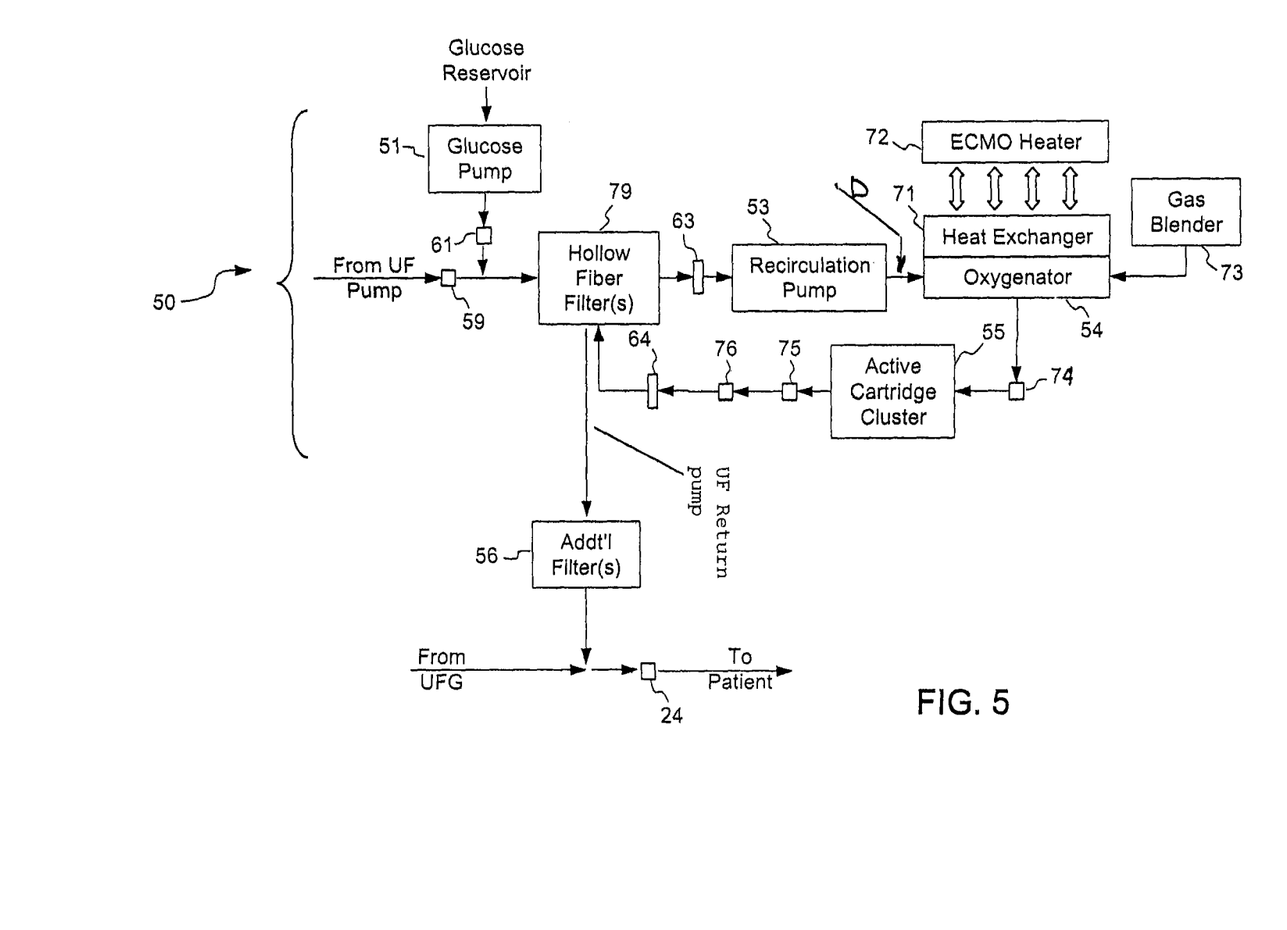
FIG. 5 is a simplified block diagram illustrating another embodiment of a recirculation circuit.

FIG. 5 is a simplified block diagram illustrating another embodiment of a recirculation circuit. The FIG. 5 embodiment may be implemented in conjunction with system 10 such as illustrated and described above with reference to FIGS. 1 and 2. In that regard, various elements represented in FIG. 5 generally correspond to those described in detail above with reference to FIG. 3, and may comprise, embody, or incorporate some or all of the functionality and the structural or operational characteristics set forth above. In particular, with respect to FIGS. 3 and 5, like reference numerals generally represent like, similar, or equivalent components embodying the foregoing attributes as well as additional features or aspects set forth below.

For example, with respect to components illustrated in FIG. 5 as well as the system 10 with which the FIG. 5 recirculation circuit 50 is employed, blood control unit 20, pumps 30 and 51, additional filters 56, and UFG 40, as well as valve assemblies 61 and 24, for example, may generally correspond to those previously described, and may operate substantially as set forth in detail above. As before, if desired, the locations of oxygenator 54 and active cartridge cluster 55 can be optionally switched.

A modified UFG 40 may be provided for use with either the FIG. 3 or the FIG. 5 recirculation circuit 50, though particular advantages may be attendant with implementation of such a modified UFG 40 in the FIG. 5 arrangement. In particular, UFG 40 may incorporate or comprise synthetic fibers (such as polysulfone, for example, or an equivalent thereof) having increased membrane permeability; these fibers may facilitate increased or improved transfer of proteins (especially albumin, having an approximate molecular weight of 68,000 Daltons) across the semi-permeable membrane. Accordingly, a modified UFG 40 may allow more efficient albumin transfer from the whole blood to the UF. In some embodiments, this efficient albumin transfer at UFG 40 may result in a greater quantity of albumin available for transfer to the therapeutic cells in active cartridges 55. Many toxins are known to bind to albumin, and UFG 40 modified to comprise polysulfone fibers may permit a higher rate of transfer of these albumin-bound toxins to the active therapeutic cells. Additionally, UFG 40 may prevent a significant amount (less than, for example, 10%) of fibrinogen (having an approximate molecular weight of 340,000 Daltons) to be transported across the membranes from whole blood to the UF. In one exemplary embodiment, a polysulfone UFG and 0.2 micron cartridges available from Minntech Corp. can be used.

In addition to compatibility with improved UFG 40 materials and fiber permeabilities targeted for specific proteins, the FIG. 5 recirculation circuit 50 may provide or incorporate some or all of the following refinements: superior hollow fiber cartridge materials and more appropriate fiber porosity; utilization of Community of Europe (CE) marked components; data acquisition, consolidation, storage, and reporting, as well as real-time or near real-time display of active cartridge metabolic data; reduced risk of contamination during set-up or initialization; open arrangement of system components; and a more efficient filtration configuration and design.

At the input to the FIG. 5 recirculation circuit 50, a detoxification device 59 may be implemented in the UF line upstream of glucose infusion pump 51. It will be appreciated that detoxification device 59 may be located elsewhere in recirculation circuit 50, depending, for example, upon the desired operational flow rate of UF through recirculation pump 53, the type and quantity of active therapeutic cells utilized in active cartridges 55, and other factors. In some embodiments, detoxification device 59 may be situated in the return line, i.e., interposed between filters 79 and the junction with the blood circuit. For example, one or more detoxification devices D can be optionally located as shown by FIG. 5. Additionally, a heat exchanger may be located in the blood return line to warm the treated whole blood prior to infusion into the patient. A cardioplegia heat exchanger from COBE CV (model CSC14, for example) may satisfy system requirements.

Reservoir 52 described above with reference to FIG. 3 may be augmented by or replaced with (as in the exemplary FIG. 5 arrangement) one or more hollow fiber filters 79. In some embodiments, filters 79 may comprise membranes having a pore size of between 0.1 and 0.2 μm (to capture microbacteria, for example), and may provide a fluid volume of UF similar to that of reservoir 52 (e.g., approximately 200 mL), accommodating or allowing differential flow rates between the blood circuit and recirculation circuit 50 as set forth above.

As in the FIG. 3 embodiment, the FIG. 5 recirculation circuit 50 may include one or more priming reservoirs 63 upstream of recirculation pump 53 to provide suitable priming fluid or combinations of fluids prior to initiation of therapy or detoxification treatments. Similarly, one or more collection bags or reservoirs 64 may collect priming fluid, for example, or allow one or more components of recirculation circuit 50 to be flushed for maintenance.

As noted above, recirculation pump 53 may be a non-CE-marked peristaltic or (roller) pump. Alternatively, a centrifugal pump may provide a safer recirculation flow (i.e., little or no over-pressurization and, consequently, less risk of burst tubing) without sacrificing accuracy or ease of operation. In that regard, at least three CE-marked centrifugal pumps currently available may satisfy system requirements: COBE CV (Revolution); Terumo Medical (Sams Centrifugal System); and Medtronic (Bio-Pump). Each of the foregoing pumps is equipped with a battery back-up as well as a sterile, magnetically coupled pump head.

On the pressure side (i.e., downstream) of recirculation pump 53, the FIG. 5 arrangement incorporates a heat exchanger 71 operative in conjunction with oxygenator 54. In some embodiments, a heater unit 72, such as a water bath and Extracorporeal Membrane Oxygenation (ECMO) heater apparatus, for example, may be coupled to heat exchanger 71, enabling or facilitating recirculation circuit 50 to maintain temperatures of the UF in active cartridges 55 at or near 37° C. Accordingly, oxygenator 54, heat exchanger 71, and heater unit 72 may generally replace heating chamber 59 implemented in the FIG. 3 configuration. Various ECMO heaters approved for medical or clinical use are currently available from Cincinnati Sub-Zero and Terumo Medical, for example.

Additionally, it is noted that insulation may sustain UF in recirculation circuit 50 at an appropriate or desired temperature, or within a prescribed temperature range. For example, a layer of removable insulation may be applied to active cartridges 55 and to the tubing and conduits between oxygenator 54 and active cartridges 55, as well as elsewhere in recirculation circuit 50.

Oxygenator 54 may be coupled to a gas blender unit 73, which may be embodied as or comprise a medical-grade gas blending device operative to supply gas to oxygenator 54. The addition of medical-grade gas blender 73 may provide simultaneous control of both the total gas flow as well as the percentage of oxygen or $FiO_2$, i.e., the oxygen concentration may be selectively adjusted to a desired level within the capabilities of gas blender 73. By way of example, an approved medical-grade gas blender is currently available from Sechrist Industries.

With respect to data acquisition and analysis, one or more in-line blood gas analyzers 74 and 75 may be implemented upstream or downstream (or both) of cartridge cluster 55. Where two gas analyzers 74,75 are arranged as illustrated in FIG. 5, oxygen and pH differentials from both the upstream and downstream sides of active cartridges 55 may provide important measurements of therapeutic cell function over time during therapy. Samples drawn from system 10 may be compared with off-line or reference measurements both to estimate instantaneous levels and to track oxygen and pH differentials over time. Such measurements and comparisons may be made in real-time using the FIG. 5 arrangement, i.e., multiple in-line analyzers 74, 75. Alternatively, a single in-line analyzer with two sets of flow-through probe chambers may be used. By way of example, one approved analyzer system which satisfies the requirements of recirculation circuit 50 is a CDI 500 apparatus available from Terumo Medical.

In the FIG. 5 arrangement, an input or infusion port 76 may be provided downstream of active cartridge cluster 55; alternatively, port may be located upstream of active cartridges 55, or even upstream of oxygenator 54, for example, depending upon the purpose and functional characteristics of the substance to be infused into the UF. In that regard, it is noted that more than one infusion port 76 may be appropriate or desired in certain situations. In some exemplary embodiments, infusion port 76 may allow induction of promoters or inducers selected and operative to enhance or to accelerate treatment (i.e., therapeutic or detoxification processes) taking place in active cartridges 55. The type, nature, and chemical composition of such promoters or inducers may be selected as a function of the active cells supported in active cartridges 55, for example. In that regard, various promoters are generally known in the art and may be operative to enhance the activity of therapeutic cells.

In the FIG. 5 active cartridge cluster 55, fibers may be synthetic, such as the polysulfone fibers described above, with a porosity of approximately 0.2 µm, for example. Synthetic fiber such as polysulfone may provide superior durability and biocompatibility relative to cellulose fibers. Higher porosity membranes may also allow essentially all molecules, including larger proteins, to pass between the UF and the active cells in the ECS of the active cartridges 55. As indicated in FIG. 5, active cartridges 55 may comprise a cluster of filters arranged either in parallel or in series.

The additional filters 56 described above with reference to FIG. 3 (i.e., in-line capsule-type filters having a pore size of approximately 0.45 µm) may be replaced by one hollow fiber cartridge having a pore size of approximately 0.1-0.2 µm and one capsule filter having a similar pore size. A hollow fiber unit, even with tighter pores, may cause lower back pressure due to significantly increased surface area (e.g., 2.0 $m^2$ versus the capsule filter having a surface area of about 0.055 $m^2$). This configuration may not only prevent contamination present in recirculation circuit 50 from crossing over to the patient's blood line, but also lengthen the time between filter changes during therapy. Suitable hollow fiber cartridges are presently available from Minntech Corp. and Spectrum Laboratories, for example.

As noted above, a detoxification device 59 may be positioned or located in a similar position as additional filters 56. In that regard, additional filters 56 may comprise or incorporate one or more detoxification devices 59, ammonia traps, or similar mechanical or chemical filtration devices generally known in the art or developed and operative in accordance with known principles.

The FIG. 5 design may reduce the number of separate tubing segments required for recirculation circuit 50, and simplify the construction and set-up accordingly. All tubing and components may be sterilized together, and the risk of a contamination during set-up may be reduced. As with the FIG. 3 embodiment, active cartridges 55 may be bundled or clustered together, and a single quick-disconnect on both the upstream and downstream sides of active cartridge cluster 55 may facilitate maintenance and replacement.

Figure 6:
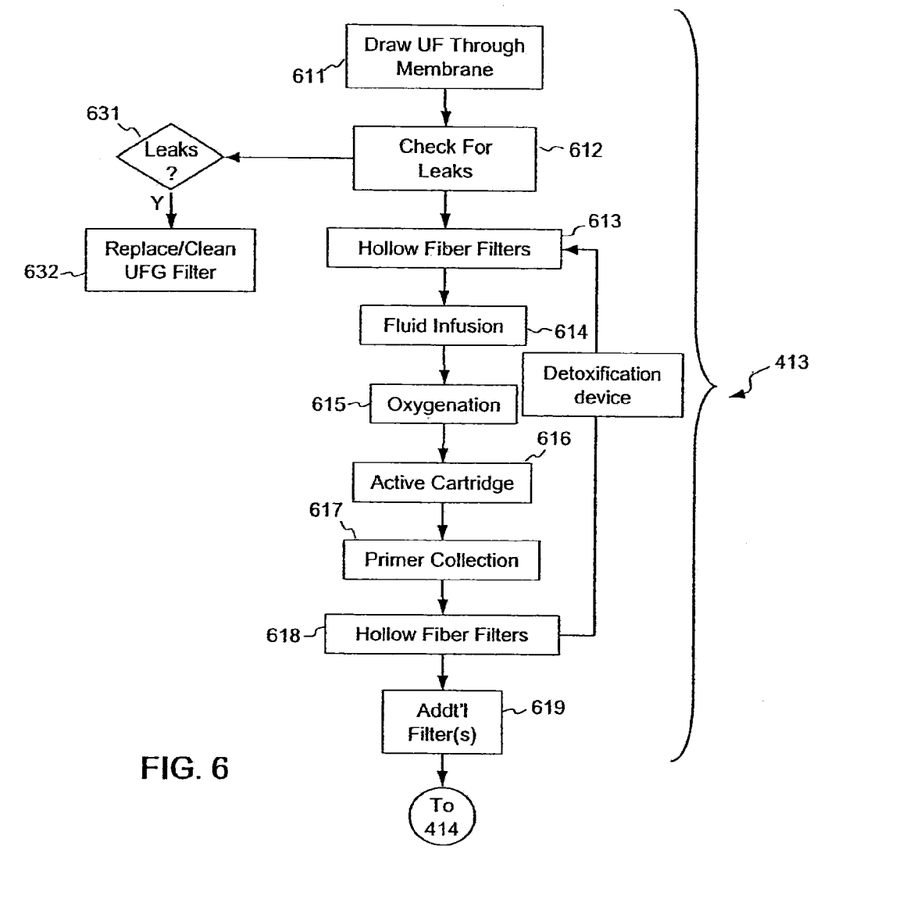
FIG. 6 is a simplified flow diagram illustrating the general operation of another embodiment of a method of extracorporeal filtration and detoxification.

FIG. 6 is a simplified flow diagram illustrating the general operation of another embodiment of a method of extracorporeal filtration and detoxification. The processes depicted in FIG. 6 are related to operation of a recirculation circuit, for example, and accordingly may be facilitated by the various components, or appropriate combinations thereof, illustrated in FIG. 5. Treating UF in accordance with the FIG. 6 method generally relates to the operation depicted at block 413 of FIG. 4A.

In that regard, drawing UF through a membrane as indicated at block 611 may represent an aspect of generating UF, such as with UFG 40, for example; accordingly, the drawing operation of block 611 may also be associated with the separating operation of block 412 in FIG. 4A. The process at block 611 is included in FIG. 6 for the sake of clarity and thoroughness. The operations depicted at blocks 612 and 632, as well as at decision block 631, may generally correspond to similarly labeled blocks illustrated and described above with reference to FIG. 4B.

With reference now to both FIGS. 5 and 6, untreated UF input to recirculation circuit 50 may be provided to hollow fiber filters 79 as indicated at block 613. Infusion of fluid (block 614) may represent introduction of glucose or other nutrients, heparin or other anticoagulation agents, promoters, enhancers, or other fluids into recirculation substantially as set forth above. It will be appreciated that the operation depicted at block 614 may occur elsewhere in the FIG. 6 embodiment, representing selected locations throughout recirculation circuit 50 of FIG. 5; methods and locations of fluid infusion such as represented at block 614 may depend upon the type and quantity of fluid to be infused, the nature and requirements of the active cells maintained in active cartridges, overall flow rate of UF through the circuit, and other system parameters.

Similarly, introduction of primer solution (not shown in FIG. 6) and the collection of primer solution at block 617 may occur where indicated or elsewhere in FIG. 6, depending, for example, upon the particular system components requiring priming. If filters 79 require priming in the FIG. 5 embodiment, for instance, priming may occur upstream thereof, additionally, primer collection at block 617 may be selectively located in recirculation circuit 50 as a function of the particular arrangement or relative orientation of system components.

UF may be oxygenated at block 615 and treated at block 616. Various aspects of the oxygenation process (e.g., pressure, partial pressures and composition of any air/gas mixture, infusion rates, and the like) at block 615 may be influenced by the quantity, density, nature, and functionality of the active cells (such as C3A cells, for example) maintained in the active cartridges and executing the treatment process at block 616. In the FIG. 5 arrangement, for example, oxygenation at block 615 may comprise receiving gaseous input in accordance with selected conditions or parameters from gas blender 73, and may occur in conjunction with heating UF using heat exchanger 71 and an ECMO heater apparatus 72.

Treating or detoxifying UF may generally occur in active cartridges at block 616. As set forth in detail above, the operational characteristics and specific chemical, biological, and other processes associated with block 616 may be influenced by, among other factors: promoters or enhancers induced into recirculation circuit 50; the intended overall operation of system 10 (i.e., the type of treatment required); operational parameters of system components such as recirculation pump 53; and so forth. Therapeutic processes at block 616 may be selectively adjusted, controlled, or otherwise manipulated in accordance with the specific hardware components implemented in recirculation circuit 50.

As set forth above with reference to the FIG. 5 recirculation circuit 50, one or more data acquisition and analysis components may be incorporated in the flow. Where in-line blood gas analyzers 74 and 75 are implemented upstream and downstream of cartridge cluster 55, for example, an analyzing operation may be executed both prior to and subsequent to treatment at block 616. In such an embodiment, oxygen and pH differentials from both the upstream and downstream sides of treatment processing may provide important measurements of therapeutic cell function over time during therapy. Such measurements, comparisons, and subsequent data processing operations may have utility both in system diagnostics applications as well as in ascertaining the efficacy or thoroughness of treatment at block 616. Data can be also acquired and analyzed with respect to flow rates, temperatures and pressures throughout the system.

Treated UF may be returned to hollow fiber filters 79 as indicated at block 618 and described in detail above. Providing (block 613) and returning (block 618) UF to filters 79 at both ends of a recirculation circuit 50 may allow or enable a system and method of treating UF to operate at a different flow rate than that maintained in the blood circuit of a treatment system 10.

Prior to recombining treated UF with cellular blood components at block 414, additional filtering may be conducted at block 619. In some embodiments described above, filtering at block 619 may include passing UF through one or more in-line cell filters, hollow fiber cartridges, ammonia traps, charcoal filters, mechanical filters, and so forth. UF which is neither processed at block 619 nor returned to the patient may be recirculated for additional treatment as represented by the loop from block 618 back up to block 613.

Those of skill in the art will appreciate that the order of operations illustrated in FIGS. 4B and 6 is provided by way of example only, and not to the exclusion of other possibilities. In particular, the present disclosure is not intended to be interpreted in any limited sense with respect to the order or sequence of events depicted in FIGS. 4B and 6.

The present invention has been illustrated and described in detail with reference to particular embodiments by way of example only, and not by way of limitation. Those of skill in the art will appreciate that various modifications to the described exemplary embodiments are within the scope and contemplation of the present disclosure. Therefore, it is intended that the invention be considered as limited only by the scope of the appended claims.

What is claimed is:

1. A system, comprising:
   (a) an ultrafiltrate generator operative to separate ultrafiltrate from cellular components of blood;
   (b) a blood control unit comprising:
      a first pump operative to circulate blood from a patient, through the ultrafiltrate generator, and back to the patient; and
      a second pump operative to draw the ultrafiltrate from the blood through the ultrafiltrate generator;
   (c) a recirculation circuit operative to treat the ultrafiltrate independently of the cellular components; and
   (d) an oxygenator operative to infuse gas into the ultrafiltrate in response to oxygen and pH differentials in the ultrafiltrate.

2. The system of claim 1, wherein said blood control unit further comprises a leak detector operative to analyze the composition of the ultrafiltrate downstream of the ultrafiltrate generator.

3. The system of claim 1, wherein the blood pump is operative to circulate the blood at a predetermined flow rate.

4. The system of claim 1, wherein the ultrafiltrate generator comprises a hollow fiber filter cartridge.

5. The system of claim 4, wherein the hollow fiber filter cartridge comprises a semi-permeable membrane having a predetermined molecular weight cut-off.

6. The system of claim 5, wherein the semi-permeable membrane has a predetermined molecular weight cut-off of about 100,000 Daltons.

7. The system of claim 5, wherein the semi-permeable membrane has a pore size of approximately 0.2 µm.

8. The system of claim 5, wherein the semi-permeable membrane has a pore size of approximately 0.1 µm.

9. The system of claim 4, wherein the hollow fiber filter cartridge comprises synthetic fibers.

10. The system of claim 9, wherein the synthetic fibers are polysulfone.

11. The system of claim 1, further comprising an anticoagulant infusion pump operative to infuse the blood with an anticoagulation agent.

12. The system of claim 11, wherein the anticoagulation agent is heparin.

13. The system of claim 1, further comprising a glucose pump operative to infuse the ultrafiltrate with glucose.

14. The system of claim 1, wherein the recirculation circuit comprises a heating chamber operative to maintain the ultrafiltrate at a predetermined temperature.

15. The system of claim 1, wherein the recirculation circuit comprises a heat exchanger operative to maintain the ultrafiltrate at a predetermined temperature.

16. The system of claim 1, wherein the recirculation circuit is configured and operative to maintain the ultrafiltrate at approximately 37° C.

17. The system of claim 1, wherein the recirculation circuit comprises an active cartridge containing active cells operative to effectuate a treatment of the ultrafiltrate.

18. The system of claim 17, further comprising a promoter infusion pump operative to infuse the ultrafiltrate with a promoter selected to enhance the activity of the active cells.

19. The system of claim 17, wherein the active cells are a subclone of the human hepatoblastoma cell line.

20. The system of claim 19, wherein the active cells are the C3A cell line.

21. The system of claim 17, wherein the recirculation circuit comprises a recirculation pump operative to circulate the ultrafiltrate through the active cartridge at a selected flow rate.

22. The system of claim 21, wherein the selected flow rate maintained by the recirculation pump differs from a flow rate maintained by the first pump in the blood control unit.

23. The system of claim 1, further comprising a conduit junction operative to recombine the ultrafiltrate with the blood prior to returning the blood to the patient.

24. The system of claim 23, further comprising a filter operative to filter the ultrafiltrate upstream of the conduit junction.

25. The system of claim 24, wherein the filter comprises a hollow fiber filter.

26. The system of claim 24, wherein the filter comprises one or more of a charcoal filter, an ammonia trap, and a mechanical filter.

27. The system of claim 1, further comprising:
a detector operative to detect gaseous contaminants in the blood; and
a mechanical filtration device operative to remove the gaseous contaminants from the blood.

28. An extracorporeal detoxification system, comprising:
(a) a blood circuit coupled to a patient and operative to communicate blood from the patient, through an ultrafiltrate generator, and back to the patient;
(b) a recirculation circuit coupled to the ultrafiltrate generator and operative to draw ultrafiltrate from the ultrafiltrate generator and to treat the ultrafiltrate independently of cellular components of the blood;
(c) a conduit junction operative to recombine the ultrafiltrate in the recirculation circuit and the cellular components in the blood circuit prior to reintroduction to the patient; and
(d) an oxygenator operative to infuse gas into the ultrafiltrate depending on the oxygen and pH differentials detected in the ultrafiltrate.

29. The system of claim 17, wherein the recirculation circuit further comprises a blood gas analyzer operative to monitor the treatment.

30. The system of claim 28, wherein the recirculation circuit comprises a leak detector operative to analyze the composition of the ultrafiltrate downstream of the ultrafiltrate generator.

31. The system of claim 28, wherein the blood circuit comprises a blood pump operative to communicate the blood at a predetermined flow rate.

32. The system of claim 28, wherein the ultrafiltrate generator comprises a hollow fiber filter cartridge.

33. The system of claim 32, wherein the hollow fiber filter cartridge comprises a semi-permeable membrane having a predetermined molecular weight cut-off.

34. The system of claim 33, wherein the semi-permeable membrane allows albumin to permeate.

35. The system of claim 33, wherein the semi-permeable membrane does not allow a majority of fibrinogen to permeate.

36. The system of claim 32, wherein the hollow fiber filter cartridge comprises synthetic fibers.

37. The system of claim 36, wherein the synthetic fibers are polysulfone.

38. The system of claim 28, further comprising an anticoagulant infusion pump operative to infuse the blood with an anticoagulation agent.

39. The system of claim 38, wherein the anticoagulation agent is heparin.

40. The system of claim 28, further comprising a glucose pump operative to infuse the ultrafiltrate with glucose.

41. The system of claim 28, wherein the recirculation circuit comprises a heating chamber operative to maintain the ultrafiltrate at a predetermined temperature.

42. The system of claim 28, wherein said recirculation circuit comprises a heat exchanger operative to maintain the ultrafiltrate at a predetermined temperature.

43. The system of claim 28, wherein the recirculation circuit comprises an active cartridge containing active cells operative to effectuate a treatment of the ultrafiltrate.

44. The system of claim 43, further comprising a promoter infusion pump operative to infuse the ultrafiltrate with a promoter selected to enhance the activity of the active cells.

45. The system of claim 43, wherein the active cells are a subclone of the human hepatoblastoma cell line.

46. The system of claim 45, wherein the active cells are the C3A cell line.

47. The system of claim 43, wherein the recirculation circuit comprises a recirculation pump operative to circulate the ultrafiltrate through the active cartridge at a selected flow rate.

48. The system of claim 47, wherein said selected flow rate maintained by the recirculation pump differs from a flow rate maintained in the blood circuit.

49. The system of claim 28, further comprising a filter operative to filter the ultrafiltrate upstream of the conduit junction.

50. The system of claim 49, wherein the filter comprises a hollow fiber filter.

51. The system of claim 49, wherein the filter comprises one or more of a charcoal filter, an ammonia trap, and a mechanical filter.

52. The system of claim 43, wherein said recirculation circuit further comprises a blood gas analyzer operative to monitor the treatment.

53. The system of claim 28, further comprising:
(d) a detector operative to detect gaseous contaminants in the blood; and
(e) a mechanical filtration device operative to remove the gaseous contaminants from the blood circuit.

* * * * *